(12) United States Patent
Rezach

(10) Patent No.: US 11,627,995 B2
(45) Date of Patent: Apr. 18, 2023

(54) LOCKING-CAP MODULE AND CONNECTOR

(71) Applicant: Warsaw Orthopedic, Inc., Warsaw, IN (US)

(72) Inventor: William A. Rezach, Covington, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 12 days.

(21) Appl. No.: 17/128,615

(22) Filed: Dec. 21, 2020

(65) Prior Publication Data

US 2022/0192715 A1 Jun. 23, 2022

(51) Int. Cl.
*A61B 17/70* (2006.01)
*A61B 17/90* (2006.01)
*A61B 90/00* (2016.01)

(52) U.S. Cl.
CPC ...... *A61B 17/7032* (2013.01); *A61B 17/7035* (2013.01); *A61B 90/08* (2016.02); *A61B 2090/0811* (2016.02)

(58) Field of Classification Search
CPC ............ A61B 17/7032; A61B 17/7035; A61B 17/7037; A61B 17/7038; A61B 17/7034; A61B 17/704; A61B 17/70; A61B 2090/0811; A61B 2090/0808
See application file for complete search history.

(56) References Cited

U.S. PATENT DOCUMENTS

| | | | |
|---|---|---|---|
| 6,540,749 B2 | 4/2003 | Schafer et al. | |
| 6,641,586 B2 | 11/2003 | Varieur | |
| 6,726,687 B2 | 4/2004 | Jackson | |
| 6,730,089 B2 | 5/2004 | Jackson | |
| 6,786,903 B2 | 9/2004 | Lin | |
| 6,918,911 B2 | 7/2005 | Biedermann et al. | |
| 7,141,051 B2 | 11/2006 | Janowski et al. | |
| 7,156,850 B2 | 1/2007 | Kim | |

(Continued)

OTHER PUBLICATIONS

CREO AMP® Stabilization System, Globus Medical, https://www.globusmedical.com/products/creo-amp/.

(Continued)

*Primary Examiner* — Jan Christopher L Merene
*Assistant Examiner* — Anna V. Little
(74) *Attorney, Agent, or Firm* — Fox Rothschild LLP

(57) ABSTRACT

A locking-cap module may include a locking-cap having a first connecting flange and a second connecting flange opposite the first connecting flange extending from a side surface of the locking-cap. The locking-cap may further include a first retaining rail and a second retaining rail opposite the first retaining rail. The locking-cap module may further include a set screw configured to engage with corresponding threads of the locking-cap. In some embodiments, the first connecting flange and second connecting flange are configured to engage with a connector such that the top surface of the locking-cap is generally flush with a top surface of the connector when the locking-cap is in a locked position relative to the connector. In some embodiments, the set screw is initially coupled to the locking-cap by a pre-loaded connection. In some embodiments, an end user may visually verify that the locking-cap module is in the locked position.

16 Claims, 10 Drawing Sheets

(56) References Cited

U.S. PATENT DOCUMENTS

| | | |
|---|---|---|
| 7,204,838 B2 | 4/2007 | Jackson |
| 7,211,086 B2 | 5/2007 | Biedermann et al. |
| 7,223,268 B2 | 5/2007 | Biedermann |
| 7,503,924 B2 | 3/2009 | Lee et al. |
| 7,530,992 B2 | 5/2009 | Biedermann et al. |
| 7,645,294 B2 | 1/2010 | Kalfas et al. |
| 7,717,939 B2 | 5/2010 | Ludwig et al. |
| 7,776,067 B2 | 8/2010 | Jackson |
| 7,896,902 B2 | 3/2011 | Jeon et al. |
| 7,955,359 B2 | 6/2011 | Matthis et al. |
| 7,967,850 B2 * | 6/2011 | Jackson ............ A61B 17/7037 606/301 |
| 7,972,364 B2 | 7/2011 | Biedermann et al. |
| 8,016,862 B2 | 9/2011 | Felix et al. |
| 8,025,680 B2 | 9/2011 | Hayes et al. |
| 8,034,086 B2 | 10/2011 | Iott et al. |
| 8,075,590 B2 | 12/2011 | Janowski et al. |
| 8,100,946 B2 | 1/2012 | Strausbaugh et al. |
| 8,123,784 B2 | 2/2012 | Biedermann et al. |
| 8,162,989 B2 | 4/2012 | Khalili |
| 8,172,876 B2 | 5/2012 | Janowski et al. |
| 8,221,469 B2 | 7/2012 | Zehnder et al. |
| 8,221,472 B2 | 7/2012 | Peterson et al. |
| 8,226,690 B2 | 7/2012 | Altarac et al. |
| 8,267,969 B2 | 9/2012 | Altarac et al. |
| 8,328,850 B2 | 12/2012 | Bernard et al. |
| 8,343,191 B2 | 1/2013 | Matthis et al. |
| 8,465,528 B2 | 6/2013 | Schumacher |
| 8,535,352 B2 | 9/2013 | Altarac et al. |
| 8,551,142 B2 | 10/2013 | Altarac et al. |
| 8,617,217 B2 | 12/2013 | Iott et al. |
| 8,679,162 B2 | 3/2014 | Strausbaugh et al. |
| 8,690,925 B2 * | 4/2014 | Biedermann ...... A61B 17/7035 606/279 |
| 8,740,946 B2 | 6/2014 | Peterson et al. |
| 8,784,455 B2 | 7/2014 | Matthis et al. |
| 8,870,927 B2 | 10/2014 | Matthis et al. |
| 8,888,820 B2 | 11/2014 | Blain et al. |
| 8,888,827 B2 * | 11/2014 | Harper ............... A61B 17/8685 606/267 |
| 8,911,478 B2 | 12/2014 | Jackson et al. |
| 8,920,470 B2 | 12/2014 | Ludwig et al. |
| 8,926,672 B2 | 1/2015 | Jackson et al. |
| 8,992,579 B1 * | 3/2015 | Gustine ............... A61B 17/705 606/278 |
| 9,089,370 B2 | 7/2015 | Biedermann et al. |
| 9,131,962 B2 | 9/2015 | Cahill et al. |
| 9,144,437 B2 | 9/2015 | Matthis et al. |
| 9,144,444 B2 | 9/2015 | Jackson |
| 9,259,254 B2 | 2/2016 | Iott et al. |
| 9,271,760 B2 | 3/2016 | Biedermann et al. |
| 9,333,010 B2 | 5/2016 | Matthis et al. |
| 9,339,302 B2 | 5/2016 | Biedermann et al. |
| 9,358,046 B2 | 6/2016 | Nichols et al. |
| 9,439,682 B2 | 9/2016 | Iott et al. |
| 9,439,700 B2 | 9/2016 | Peterson et al. |
| 9,498,254 B2 | 11/2016 | Spratt et al. |
| 9,554,829 B2 | 1/2017 | Cahill et al. |
| 9,655,650 B2 | 5/2017 | Blain et al. |
| 9,655,652 B2 | 5/2017 | Biedermann et al. |
| RE46,431 E | 6/2017 | Jackson |
| 9,743,957 B2 | 8/2017 | Jackson |
| 9,782,204 B2 | 10/2017 | Spratt et al. |
| 9,848,918 B2 | 12/2017 | Strausbaugh et al. |
| 9,855,076 B2 | 1/2018 | Nichols et al. |
| 9,918,747 B2 | 3/2018 | Spratt et al. |
| 9,936,979 B2 | 4/2018 | Peterson et al. |
| 9,968,378 B1 | 5/2018 | Johnson et al. |
| 9,980,754 B2 | 5/2018 | Harper et al. |
| 10,004,541 B1 | 6/2018 | Jackson |
| 10,058,354 B2 | 8/2018 | Jackson et al. |
| 10,226,282 B2 | 3/2019 | Spratt et al. |
| 10,245,077 B2 | 4/2019 | Jackson |
| 10,245,078 B2 | 4/2019 | Jackson |
| 10,265,102 B2 | 4/2019 | Jackson et al. |
| 10,285,738 B1 * | 5/2019 | Doubler ............ A61B 17/7037 |
| 10,368,917 B2 | 8/2019 | Mishra et al. |
| 10,575,877 B2 | 3/2020 | Harper et al. |
| 10,603,081 B2 | 3/2020 | Harper et al. |
| 10,639,077 B2 | 5/2020 | Nichols et al. |
| 10,687,855 B2 | 6/2020 | Jackson et al. |
| 10,709,479 B2 | 7/2020 | Keyer et al. |
| 10,751,095 B2 | 8/2020 | Jackson |
| 2007/0118123 A1 * | 5/2007 | Strausbaugh ...... A61B 17/7032 606/272 |
| 2007/0167949 A1 | 7/2007 | Altarac et al. |
| 2007/0260246 A1 | 11/2007 | Biedermann |
| 2008/0183215 A1 * | 7/2008 | Altarac ............... A61B 17/7005 606/301 |
| 2008/0294202 A1 * | 11/2008 | Peterson ............. A61B 17/7037 606/305 |
| 2009/0062866 A1 | 3/2009 | Jackson |
| 2009/0204155 A1 | 8/2009 | Aschmann |
| 2012/0239091 A1 | 9/2012 | Biedermann et al. |
| 2012/0283787 A1 | 11/2012 | Yuan et al. |
| 2013/0060294 A1 * | 3/2013 | Donahue ............ A61B 17/7032 606/308 |
| 2013/0096618 A1 | 4/2013 | Chandanson et al. |
| 2014/0052190 A1 | 2/2014 | Biedermann et al. |
| 2014/0214084 A1 | 7/2014 | Jackson et al. |
| 2014/0350607 A1 * | 11/2014 | Biedermann ...... A61B 17/7032 606/279 |
| 2015/0119942 A1 | 4/2015 | Jackson et al. |
| 2017/0209178 A1 | 7/2017 | Cahill et al. |
| 2017/0303971 A1 * | 10/2017 | Mishra ............... A61B 17/7035 |
| 2018/0263665 A1 | 9/2018 | Yacoub et al. |
| 2019/0209213 A1 | 7/2019 | Spratt et al. |
| 2020/0205862 A1 | 7/2020 | Nichols et al. |
| 2020/0253644 A1 | 8/2020 | Biedermann |
| 2021/0298791 A1 | 9/2021 | May et al. |

OTHER PUBLICATIONS

Globus Revere, <https://www.globusmedical.com/products/revere/>.

Globus Protex, https://www.globusmedical.com/products/protex/.

DePuy AcroMed, Monarch Spine System, https://www.youtube.com/watch?v=OpJj-T04Xuwg.

Pangea Degenerative Spine System Technique Guide, Synthes Spine, http://synthes.vo.llnwd.net/o16/LLNWMB8/INT%20Mobile/Synthes%20International/Product%20Support%20Material/legacy_Synthes_PDF/DSEM-SPN-0115-0250-2_LR.pdf.

Expedium® 5.5 Titanium Surgical Technique, Expedium Spine System, DePuy Synthes, http://synthes.vo.llnwd.net/o16/LLNWMB8/INT%20Mobile/Synthes%20International/Product%20Support%20Material/legacy_Synthes_PDF/105717.pdf.

Exactech (Vertiflex) Silverbolt, https://www.youtube.com/watach?v=RP9X72FOFLE.

* cited by examiner

LOCKING-CAP MODULE AND CONNECTOR

FIELD

The present technology is generally related to locking-caps and set screws configured to secure a longitudinal rod within a passageway of a construct. Disclosed locking-caps may utilize flanges that are nested within corresponding recesses of the connector and are generally flush fit with a top of the connector. Additionally, disclosed locking-caps may feature a locking tab to ensure and visually verify that the locking-cap is in the appropriate engaged position, for example. In some embodiments, the construct may be secured to a patient vertebrae via a pedicle screw or the like, for example.

BACKGROUND

Conventional connectors may be secured to a patient vertebrae via a pedicle screw and include a passageway for securing a longitudinally extending rod. At least one type of connector may be referred to as a "tulip head" connector in the relevant art field. In order to secure the longitudinally extending rod to the connector, a set screw is typically used. Conventional set screws have an inherent limitation in that they may increase the height of the construct due to requiring a certain distance of threads to maintain sufficient mechanical clamping force on the longitudinal rod. For example, a set screw and connector may require a certain amount of engaged threads to sufficiently secure the longitudinal rod in the passageway of the connector and this type of fixation may adversely impact the height of the connector and the strength of a connection between the connector and an anchoring member.

SUMMARY

The techniques of this disclosure generally relate to a locking-cap and set screw configured to retain a longitudinal rod within a passageway of a connector, for example. In some embodiments, the locking-cap mates with a corresponding connecting portion of the connector such that uppermost surfaces of flanges of the locking-cap are flush with adjacent top surfaces of the connector, for example. Additionally, in some embodiments, the locking-cap and set screw may be coupled together by a pre-loaded connection. For example, the locking-cap may be rotated into a locked position with the connector by turning only the set screw due to the pre-loaded connection. After the locking-cap is positioned into the locked position, an end user may continue turning the set screw and overcome the pre-loaded connection to advance the set screw and fully secure the longitudinal rod within the passageway of the connector.

In one aspect, the present disclosure provides a locking-cap module. The module may include a locking-cap having an internal circumferential surface having a first thread pattern, and a first connecting flange and a second connecting flange opposite the first connecting flange, for example. In some embodiments, the first and second connecting flanges extend from a side surface of the locking-cap and define, at least partly, a top surface of the locking-cap, for example. The locking-cap may further include a first retaining rail and a second retaining rail opposite the first retaining rail, the first and second retaining rails may extend from the side surface of the locking-cap and define, at least partly, a bottom surface of the locking-cap, for example. The locking-cap module may further include a set screw having an external circumferential surface having a second thread pattern. The second thread pattern may correspond in size and shape to the first thread pattern for mating with the first thread pattern, for example. In some embodiments, the first connecting flange and second connecting flange are configured to engage with a connector such that the top surface of the locking-cap is generally flush with a top surface of the connector when the locking-cap is in a locked position relative to the connector.

In another aspect, the disclosure provides that the first connecting flange includes a first locking feature and the second connecting flange includes a second locking feature, for example.

In another aspect, the disclosure provides that the first locking feature comprises a first curved outdent and the second locking feature comprises a second curved outdent, for example.

In another aspect, the disclosure provides that when the locking-cap is engaged with the connector in the locked position, the first locking feature and second locking feature are visibly verifiable to an end user as being in the locked position, for example.

In another aspect, the disclosure provides that the connector includes a first indent and a second indent, the first indent may correspond in size and shape to the first outdent to engage the first outdent, and the second indent may correspond in size and shape to the second outdent to engage the second outdent, for example.

In another aspect, the disclosure provides that the set screw and the locking-cap are initially coupled together by a pre-loaded connection, for example.

In another aspect, the disclosure provides that the pre-loaded connection is sufficient to allow the locking-cap to be tightened into the locked position by engaging and rotating the set screw, for example.

In another aspect, the disclosure provides that the first thread pattern and second thread pattern comprise a run-out-portion, and the run-out-portion is configured to prevent the set screw from threading through the locking-cap, for example.

In another aspect, the disclosure provides that the run-out-portion is further configured to maintain the set screw in an optimal position to retain a longitudinal rod extending through a rod passageway of the connector, for example.

In another aspect, the disclosure provides for a locking-cap system. The locking-cap system may include a locking-cap having an internal circumferential surface having a first thread pattern, and a first connecting flange and a second connecting flange opposite the first connecting flange. The first and second connecting flanges may extend from a side surface of the locking-cap and define, at least partly, a top surface of the locking-cap, for example. The locking-cap may further include a first retaining rail and a second retaining rail opposite the first retaining rail, the first and second retaining rails may extend from the side surface of the locking-cap and define, at least partly, a bottom surface of the locking-cap, for example. The system may further include a set screw, the set screw may include an external circumferential surface having a second thread pattern, and the second thread pattern may correspond in size and shape to the first thread pattern for mating with the first thread pattern, for example. The system may further include a connector having an internal surface including a rod passageway and a connecting portion, for example. The connecting portion may be disposed proximate an upper surface of the connector and configured to selectively couple with the locking-cap such that the locking-cap is fixed relative to the connecting portion in a locked position, for example. In some embodiments, the connecting portion may include a first connecting channel and a second connecting channel opposite the first connecting channel, and the first connecting channel may be configured to connect with the first connecting flange and the second connecting channel may be configured to connect with the second connecting flange, for example. In some embodiments, the connecting portion may further include a third connecting channel and a fourth connecting channel opposite the third connecting channel, the third connecting channel may be configured to connect with the first retaining rail and the fourth connecting channel may be configured to connect with the second retaining rail, for example. In some embodiments, when in the locked position, an upper surface of the first connecting flange and an upper surface of the second connecting flange are generally flush with corresponding upper surfaces of the connector, respectively, for example.

In another aspect, the disclosure provides that the first connecting flange may include a first locking feature and the second connecting flange may include a second locking feature, for example.

In another aspect, the disclosure provides that the first locking feature includes a first curved outdent and the second locking feature includes a second curved outdent, for example.

In another aspect, the disclosure provides that when the locking-cap may be engaged with the connector in the locked position, the first locking feature and second locking feature are visibly verifiable to an end user as being in the locked position, for example.

In another aspect, the disclosure provides that the first connecting portion of the connector may include a first indent and the second connecting portion of the connector may include a second indent. Additionally, the first indent may correspond to the first outdent in size and shape for engaging with the first outdent, and the second indent may correspond in size and shape to the second outdent for engaging with the second outdent, for example. In some embodiments, when in the locked position, the first curved outdent may be mated with the first indent and the second curved outdent may be mated with the second indent, for example.

In another aspect, the disclosure provides that the set screw and the locking-cap may be initially coupled together by a pre-loaded connection, for example.

In another aspect, the disclosure provides that the pre-loaded connection is sufficient to allow the locking-cap to be tightened into the locked position by engaging and rotating the set screw.

In another aspect, the disclosure provides that the first thread pattern and second thread pattern may comprise a run-out-portion, and the run-out-portion may be configured to prevent the set screw from threading through the locking-cap, for example.

In another aspect, the disclosure provides that the locking-cap system may further include a longitudinal rod, a crown, and an anchoring member, for example. The connector may be secured to the anchoring member and the longitudinal rod may extend through the rod passageway, for example. The crown may facilitate positioning of the longitudinal rod in the rod passageway, and the run-out-portion may be configured to maintain the set screw in an optimal position to retain the longitudinal rod with an optimal force, for example.

In another aspect, the disclosure provides a method for engaging a two piece locking-cap module with a connector. The method may include the step of providing a locking module comprising a locking-cap and a set screw, and the set screw may be operably coupled with the locking-cap by a preloaded connection, for example. The locking-cap may include a first connecting flange and a second connecting flange opposite the first connecting flange, the first and second connecting flanges may extend from a side surface of the locking-cap and define, at least partly, a top surface of the locking-cap, for example. The locking-cap may further include a first retaining rail and a second retaining rail opposite the first retaining rail, the first and second retaining rails may extend from the side surface of the locking-cap and define, at least partly, a bottom surface of the locking-cap, for example. The method may further include the step of providing a connector, and the connector may include an internal surface comprising a rod passageway and a connecting portion, for example. The connecting portion may be disposed proximate an upper surface of the connector and be configured to couple with the locking-cap such that the locking-cap is fixed relative to the connecting portion in a locked position, for example. The connecting portion may include a first connecting channel and a second connecting channel opposite the first connecting channel, and the first connecting channel may be configured to connect with the first connecting flange and the second connecting channel may be configured to connect with the second connecting flange, for example. The connecting portion may further include a third connecting channel and a fourth connecting channel opposite the third connecting channel, the third connecting channel may be configured to connect with the first retaining rail and the fourth connecting channel may be configured to connect with the fourth retaining rail, for example. The method may further include the step of rotating the locking-cap module, via a drive interface of the set screw, into the locked position thereby fixing the locking-cap relative to the connector such that an upper surface of the first connecting flange and an upper surface of the second connecting flange are generally flush with corresponding upper surfaces of the connector, respectively, for example. The method may further include the step of rotating the set screw, after the locking-cap is fixed relative to the connector, with sufficient force to overcome the pre-loaded connection.

In another aspect, the disclosure provides for a method including the installation of an anchoring member in a boney structure of a patient, and securing the connector to the anchoring member, for example. The method may further include the steps of positioning a crown within the connector and positioning a longitudinal rod within a rod passageway of the connector on top of the crown, for example. The method may further include the step of rotating the set screw, after overcoming the pre-loaded connection, thereby securing the longitudinal rod with the rod passageway, for example.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

A locking-cap for securing a connector to a longitudinal rod and a pedicle screw is disclosed. The locking-cap may include a pair of connecting flanges and a pair of retaining rails that are configured to be retaining within corresponding retaining channels of a connector. Additionally, the locking-cap may include a pair locking features that secure the locking-cap in a locked position relative to the connector. Furthermore, the pair of locking flanges may engage with the connector at a connecting portion of the connector such that the top surface of the locking-cap is generally flush with the top surface of the connector in the locked position. As used throughout this disclosure, the term "flush" shall have its ordinary technical meaning that a first component or surface is even or level relative to a second component or surface. Additionally, as used throughout this disclosure, the phrase "generally flush" is intended to clarify that such components or surfaces need not be exactly flush but rather are substantially flush allowing for such deviations that may occur due to, for example, manufacturing tolerances and/or modestly different design geometries and/or elevations that are slightly off flush yet have the same and/or similar functionality as would be understood by a person having ordinary skill in the relevant art. In some embodiments, the locking-cap may be initially coupled to a set screw by a pre-loaded connection. At least one object of the present disclosure is to provide a connector having an overall height that is relatively less than other connectors due to the particular geometry and structural features of the locking-cap.

Figure 1:
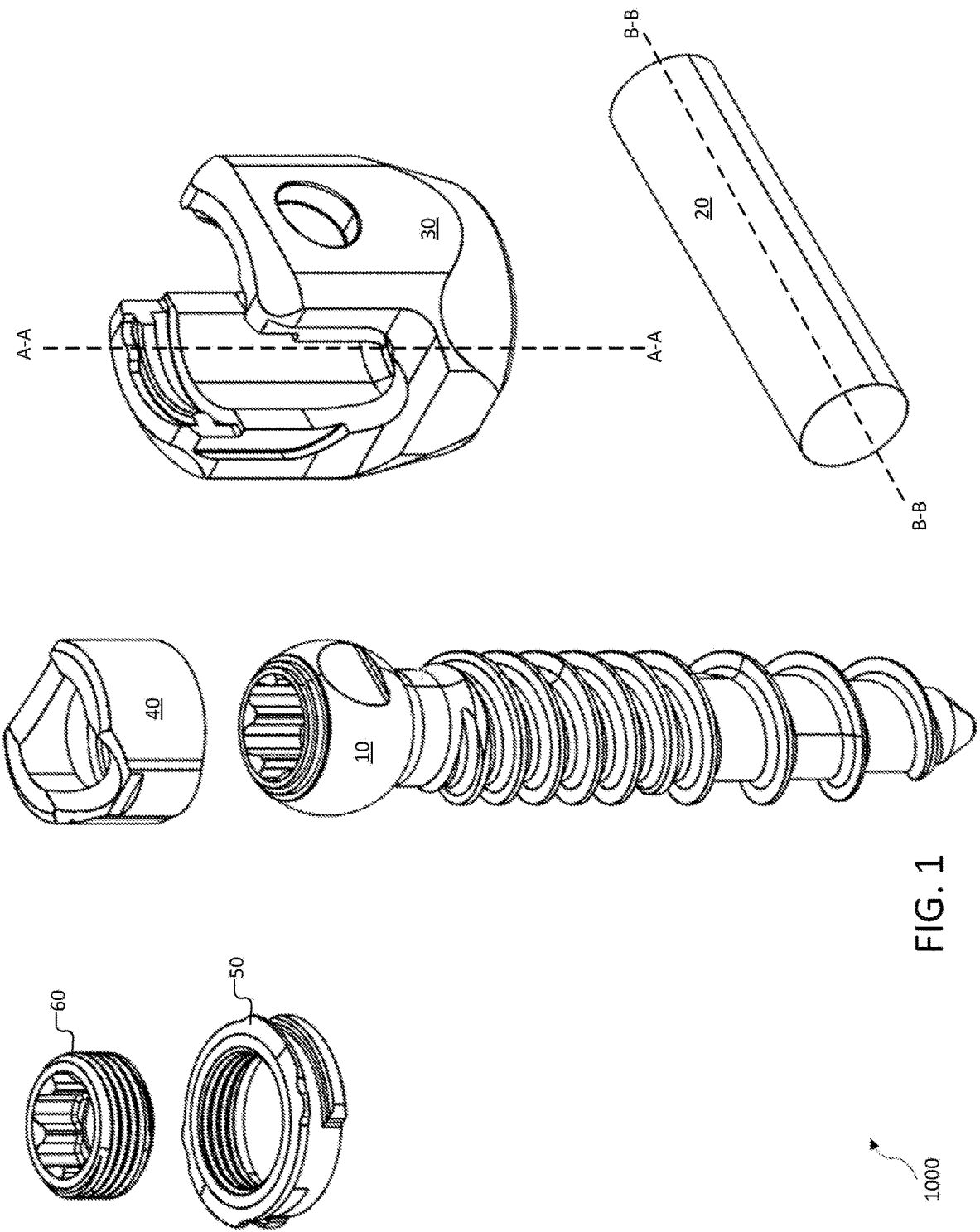
FIG. 1 is an exploded parts diagram of example components of a locking-cap system including a connector and an anchoring member.
Figure 2:
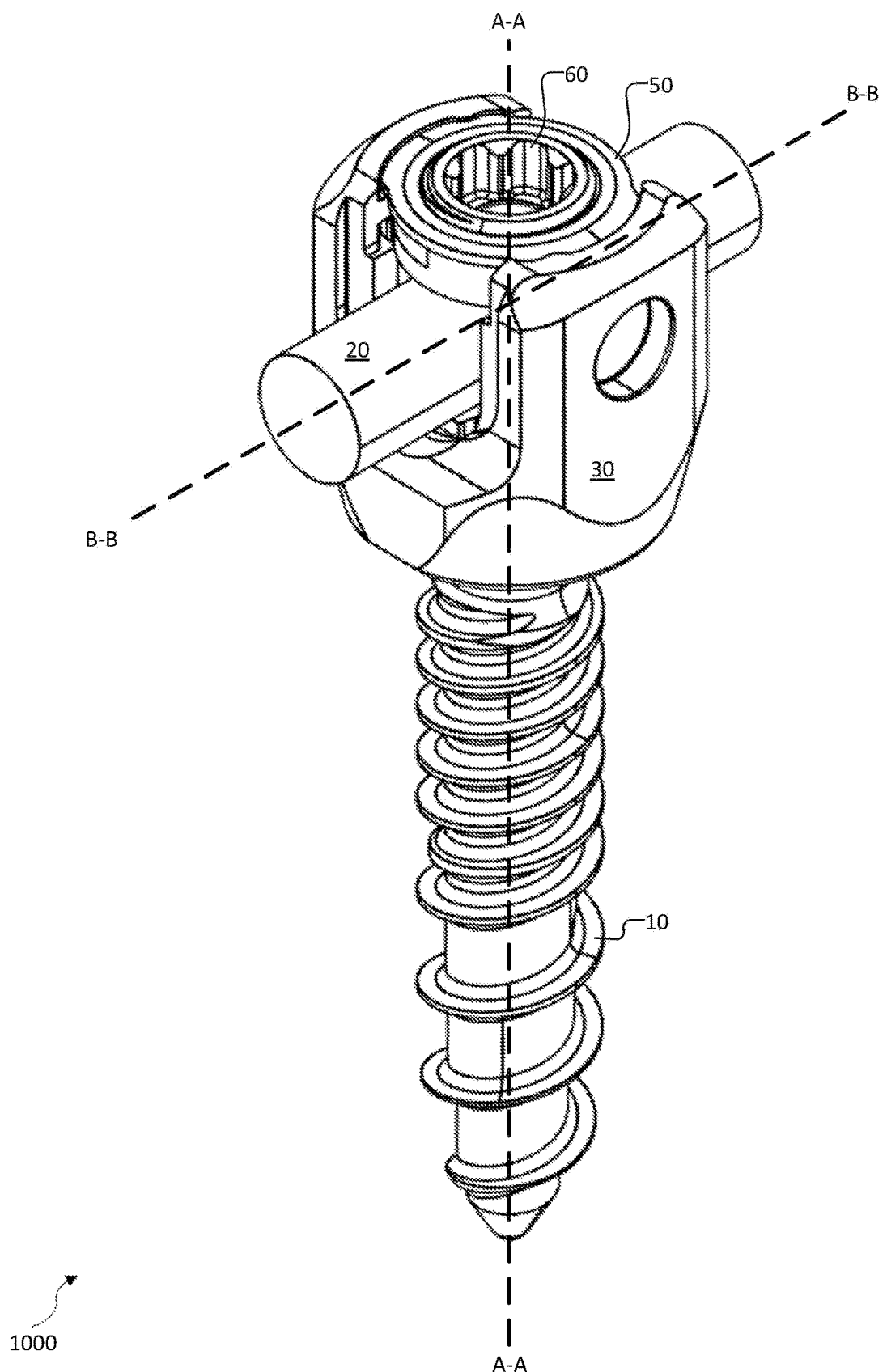
FIG. 2 is an assembled parts perspective view of an example locking-cap system including a connector and an anchoring member.

FIG. 1 is an exploded parts diagram of example components of a locking-cap system 1000. The locking-cap system 1000 may include a locking-cap 50, a crown 40, a set screw 60, a connector 30, a longitudinal rod 20, and an anchoring member 10. FIG. 2 is an assembled parts perspective view of an example locking-cap system 1000. In the illustrated embodiment, a set screw 10 may be positioned within an internal receiving cavity of a connector 30, for example. A crown 40 may be positioned over the head portion of the anchoring member 10 in axial alignment with a first axis A-A defined by the connector 30. The anchoring member 10 may be a pedicle screw, for example a multi axial screw or a uniaxial screw. Similarly, crown 40 may be any suitable type depending on the particular type of anchoring member 10. For example, the crown 40 may be configured for use with a multi axial screw (anchoring member 10) or configured for use with a uniaxial screw (anchoring member 10).

In practice a surgeon may install anchoring member 10 into a bone structure such as a patient vertebrae, for example. The anchoring member 10 may extend through an internal receiving cavity of connector 30 into the boney structure such that the connector 30 may be positioned over and around the head of anchoring member 10. The surgeon may also install the crown 40 over the head portion of anchoring member 10. The crown 40 may be axially aligned with axis A-A of the connector. Next, a surgeon may insert a longitudinal rod 20 into a rod passageway of the connector 30. The rod 20 and connector 30 may be further positioned with respect to anchoring member 10 by the use of a reduction instrument (not illustrated), for example. The rod 20 may define an axis B-B and when the rod 20 is installed within the rod passageway of the connector 30, the rod may extend in a direction that is substantially perpendicular to axis A-A. Next, a surgeon may secure the rod 20 with respect to the connector 30 by installing a locking-cap module 100. Locking-cap module 100 (see FIG. 4) may include the locking-cap 50 and the set screw 60. In some embodiments, the set screw 60 may be initially coupled to the locking-cap 50 by a pre-loaded connection, for example. Further details of the locking-cap system 1000 will be discussed below, e.g., further discussion regarding to the installation of the locking-cap 50 and set screw 60 relative to the connector 30 are discussed below with respect to FIGS. 6A-10.

Figure 3A:
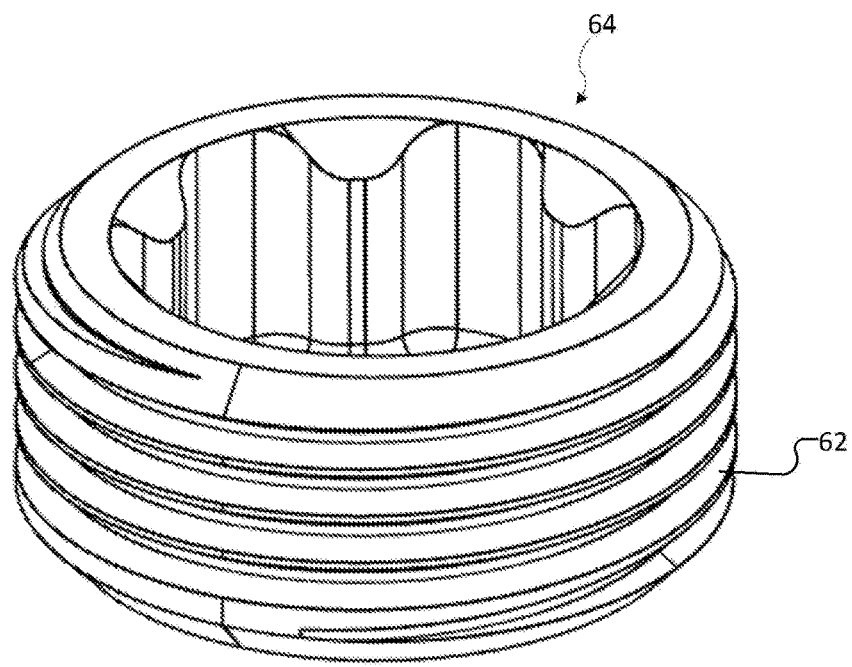
FIG. 3A is a perspective view of an example set screw.
Figure 3B:
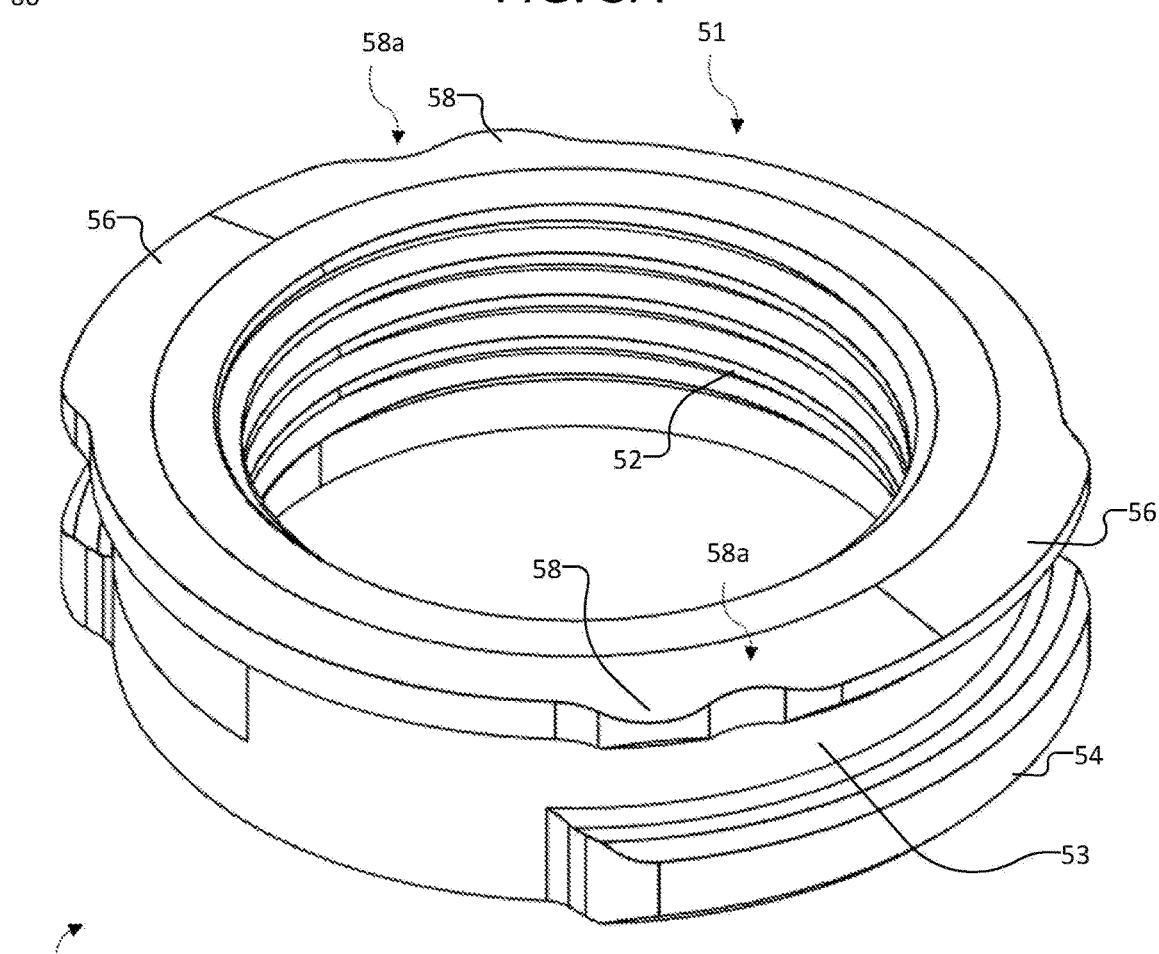
FIG. 3B is a perspective view of an example locking-cap.

FIG. 3A is a perspective view of an example set screw 60 and FIG. 3B is a perspective view of an example locking-cap 50. Set screw 60 may include a thread pattern 62 on an external circumferential surface thereof. The set screw 60 may also include a drive feature 64, that is accessible to a driver (not illustrated) from a top portion of the set screw 60, for example. In the illustrated embodiment, drive feature 64 may be configured for a hexalobular head driver, although other designs are contemplated. For example, drive feature 64 may resemble the geometry of the tip of a torx driver, hex driver, phillips driver, square head driver, hexalobular driver, polygonal driver, or the like.

Locking-cap 50 may include an opening 51 exposing an internal sidewall surface having a thread pattern 52. The opening 51 and thread pattern 52 may be configured to receive set screw 60 therein. For example, the size of the set screw 60 corresponds to the size of the opening 51 and the threads of thread pattern 62 of the set screw correspond to the threads of thread pattern 52 of the locking-cap. The locking-cap 50 may include a plurality of connecting flanges 56, for example. In the illustrated embodiment, a pair of connecting flanges 56 is shown and top surfaces of the connecting flanges define, at least partly, a top surface of the connector 50. Other embodiments may include additional connecting flanges 56, for example three or four connecting flanges depending on the chosen design. Connector 50 may further include at least one locking feature 58. In the illustrated embodiment, a pair of locking features 58 is illustrated where each locking feature 58 is adjacent to a corresponding connecting flange 56. The locking feature 58 may take any suitable shape and in the illustrated embodiment locking feature 58 is shaped like a curved outdent extending laterally from a side surface of connector 50, for example. In various embodiments, locking feature 58 may take various geometrical shapes such as, for example, oval, teardrop, tapered, chamfered, etc. Proximate the locking feature 58, connector 50 may include a curved indent 58a. In various embodiments, curved indent 58a may take various geometrical shapes such as, for example, oval, teardrop, tapered, chamfered, etc. In various embodiments, the curvature of the locking feature 58 may correspond to the curvature of the indent 58a in size and shape to snuggly engage with one another and/or engage tightly, for example. In the illustrated embodiment, an upper surface of connector 50 may be defined, at least partly, by flanges 56 that extend laterally from side surfaces of the connector 50 and adjoin the indent 58a which in turn adjoins the locking feature 58. In plan view, the flanges 56, indent 58a, and locking feature 58 define, at least partly, a portion of the perimeter of the top surface of locking-cap 50, for example. Similarly, the flanges and locking feature are generally flush with a top surface of connector 50. For example, top surfaces of the connector 50, flanges 56, and locking feature 58 are coplanar or substantially coplanar.

Connecting flange 50 may further include a plurality of retaining rails 54, for example. In the illustrated embodiment, a pair of retaining rails 54 is shown extending laterally from an outside side surface of connector 50 adjacent a bottom portion of connector 50 as an example. Other embodiments may include additional retaining rails 54, for example three or four retaining rails 54 depending on the chosen design. Additionally, retaining rails 54 may have a varying cross-sectional height and/or thickness. For example, in some embodiments, retaining rail 54 may be thickest nearest the flat portion of the side surface of connector 50 (nearest a center of connector 50) and gradually thin out approaching the vertical sidewall surface of the corresponding retaining rail 54. In the disclosed embodiment, in plan view, the connecting flange 56 and locking feature 58 are disposed above a corresponding retaining rail 54 and define, therebetween, a smooth sidewall portion that is recessed relative to the outermost side surfaces of the connecting flange 56 and retaining rail 54. For example, connector 50 may include a smooth recessed portion 53 spaced between and defined by, at least partly, a corresponding connecting flange 56 and retaining rail 54.

Figure 4:
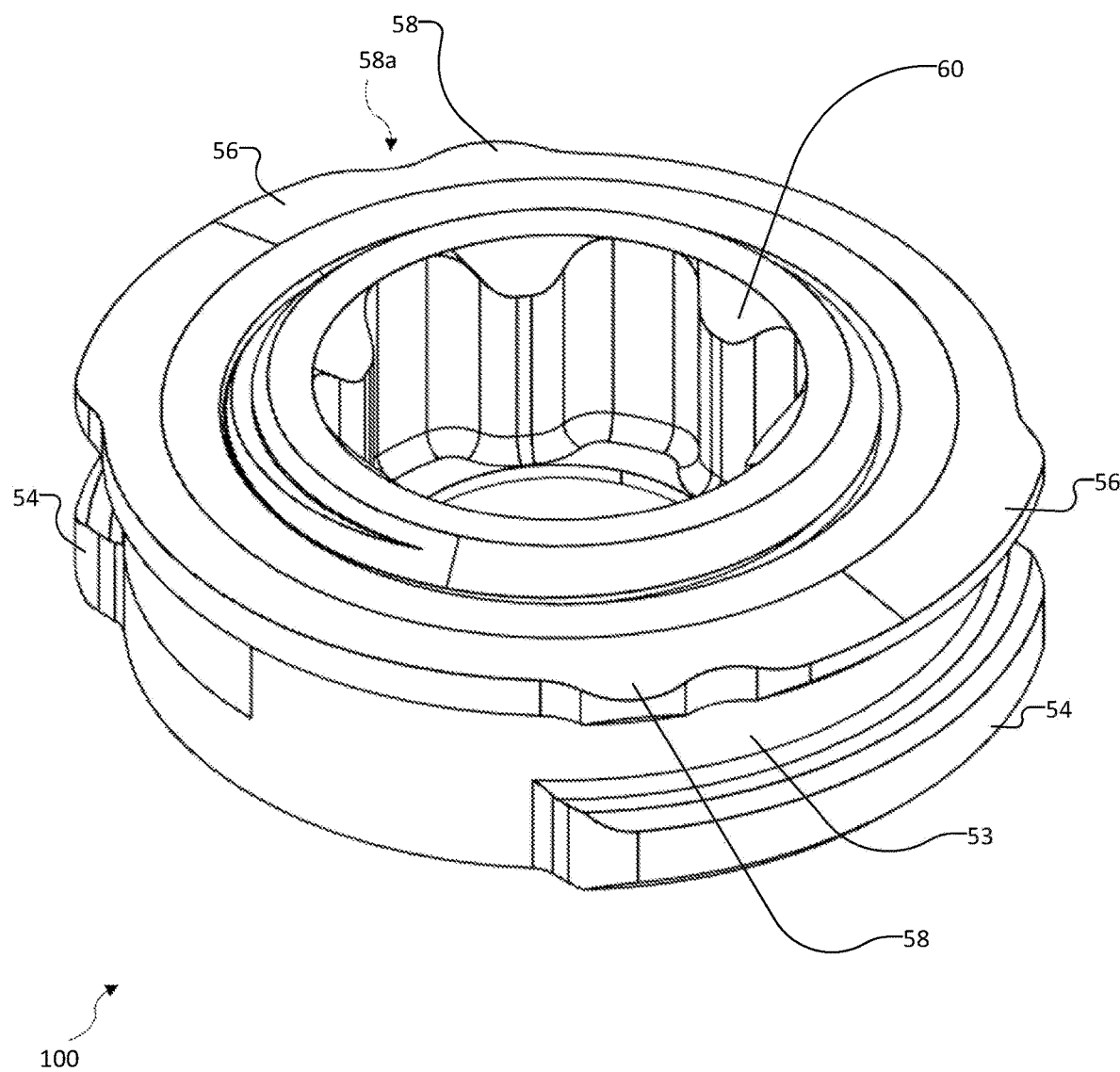
FIG. 4 is a perspective view of a pre-assembled locking-cap and set screw.

FIG. 4 is a perspective view of a pre-assembled locking-cap module 100, including a locking-cap 50 and a set screw 60. In the illustrated embodiment, the set screw 60 is engaged with the locking-cap 50 via thread patterns 52 and 62, for example. In some embodiments, it may be advantageous to initially couple set screw 60 to locking-cap 50 by a pre-loaded connection. An example pre-loaded connection may fixedly couple the set screw 60 to locking-cap 50. Additionally, the pre-loaded connection may be configured to be severed, or otherwise broken, when a sufficient force is applied to set screw 60 relative to connector 50, for example. In at least one embodiment, the pre-loaded connection may comprise at least one tac weld or surface weld at a portion of locking-cap module 100 where set screw 60 and connector 50 contact one another. For example, a precisely sized and dimensioned laser welded seam or point at a junction between set screw 60 and connector 50 on a bottom surface or on an upper surface. Other embodiments may utilize an adhesive or an epoxy as a functional equivalent. In at least embodiment, the pre-loaded connection may be designed to sustain a maximum force, i.e., the pre-loaded connection may be configured to sever or break at a pre-determined design load. For example, when a sufficient rotational force is applied to set screw 60 relative to locking-cap 50 the pre-loaded connection may sever and the set screw 60 can, thereafter, rotate relative to connector 50 via threads 52, and 62. In at least one embodiment, the pre-load connection is about 35 inch lbs., although this number may be adjusted based on the particular design criteria and/or preferences of a surgeon, for example.

Figure 5:
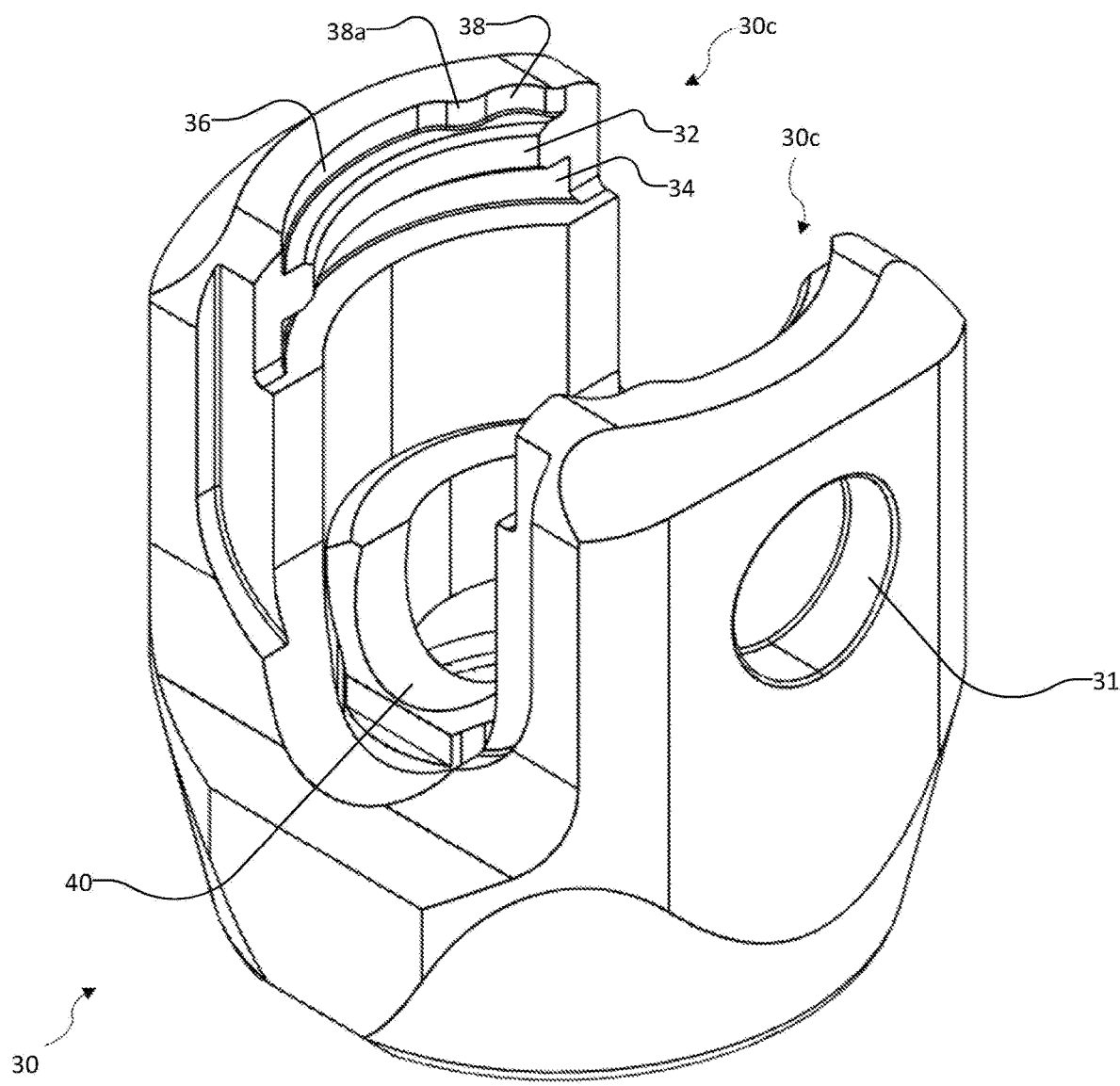
FIG. 5 is a perspective view of an example connector.

FIG. 5 is a perspective view of an example connector 30 and an example crown 40 positioned within the connector 30. In the illustrated embodiment, connector 30 may include a plurality of arm portions 30a, 30b which may define, at least partly, side surface of connector 30. In the example embodiment, a first arm portion 30a and a second arm portion 30b are disclosed. Each arm portion 30a, 30b, may include at least one gripping portion 31 disposed on an exposed side surface of connector 30. The gripping portion 31 may be configured such that a reduction instrument or other surgical tool may rigidly hold onto connector 30 for positioning of the connector 30 and/or to reduce or properly position a longitudinal rod 20 within a rod passageway of connector 30. Each arm portion 30a, 30b may include and/or otherwise define an upper surface 33 of connector 30, at least partly, for example.

Each arm portion 30a, 30b, may include a corresponding connecting portion 30c, for example. Each connecting portion 30c may be configured to connect with corresponding features of locking-cap 50, for example. In the illustrated example embodiment, connection portion 30c may be disposed proximate an upper portion of connector 30 on exposed interior side surfaces thereof. Each connecting portion 30c may include a connecting rail 32, a lower channel 34, and an upper channel 36, for example. The connecting rail 32 may protrude laterally from an internal side surface of a corresponding arm portion 30a and 30b, for example, and thereby define the lower channel 34 and upper channel 36. The upper channel 36 may be further defined by and/or considered to include a curved indent 38 and a curved outdent 38a, for example. In some embodiments, the curvature of the indent 38 may correspond to the curvature of the outdent 38a, for example.

Figure 6A:
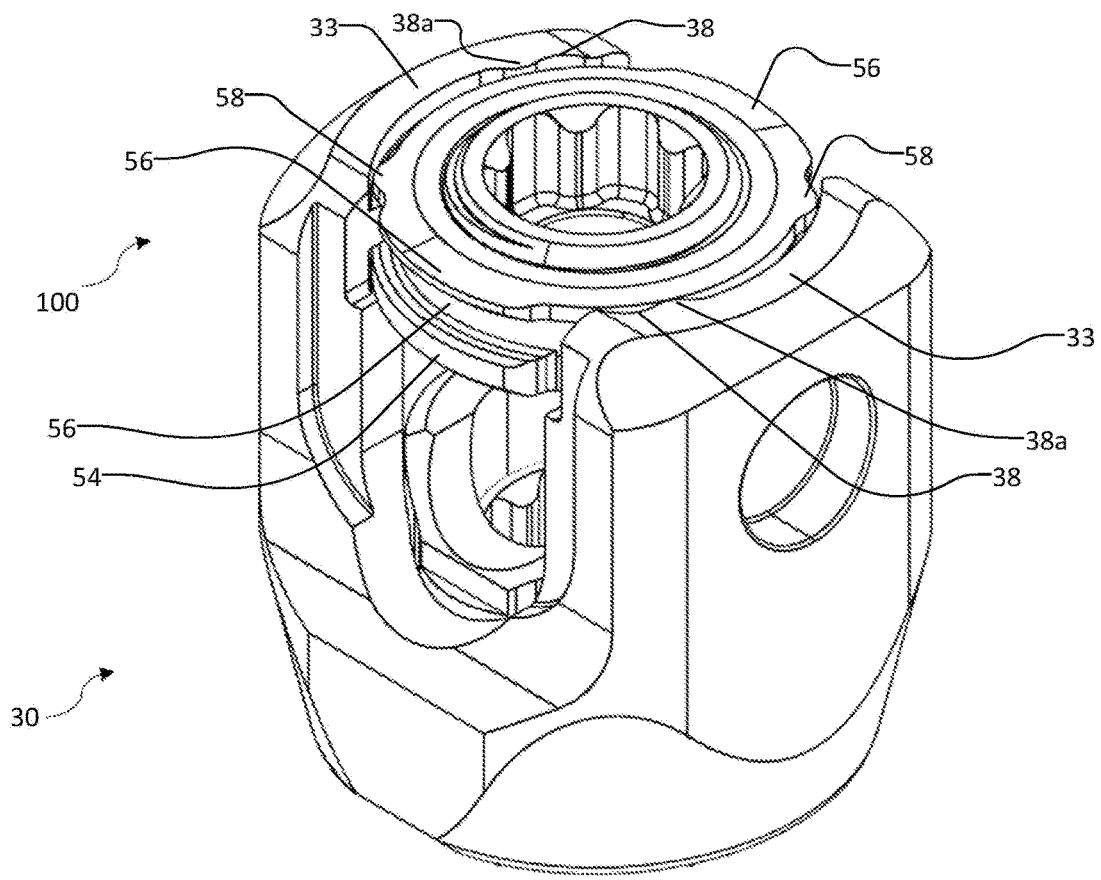
FIG. 6A is a perspective view of an example locking-cap system in an initial position before being engaged in a locking position.
Figure 6B:
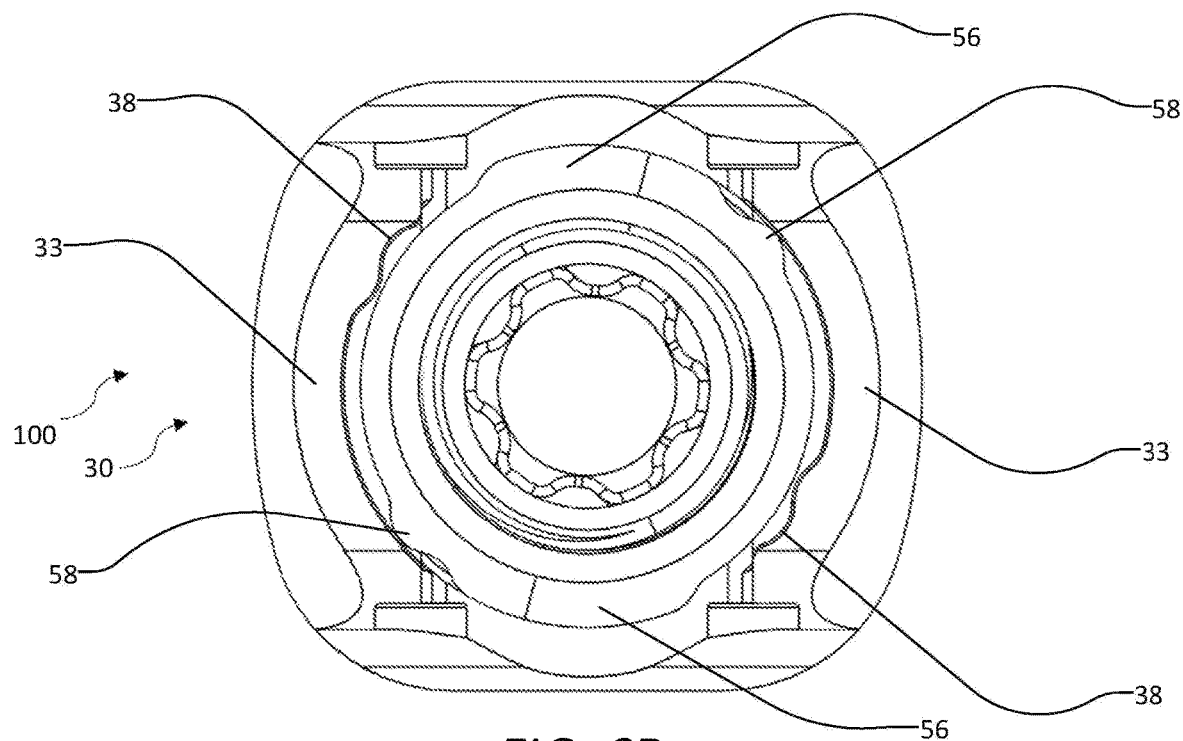
FIG. 6B is a top down view of an example locking-cap system in an initial position before being engaged in a locking position.

FIG. 6A is a perspective view of an example locking-cap module 100 in an initial position (a non-tightened position) before being engaged in a locking position (a tightened position). FIG. 6B is a top down view of an example locking-cap module 100 in an initial position before being engaged in a locking position. As illustrated, the locking-cap module 100 is positioned between arms 30a and 30b in an initial position, for example. In the initial position, the rails 54, connecting flanges 56, and locking feature 58 may not be engaged with the connecting portion 30c of connector 30.

Figure 7A:
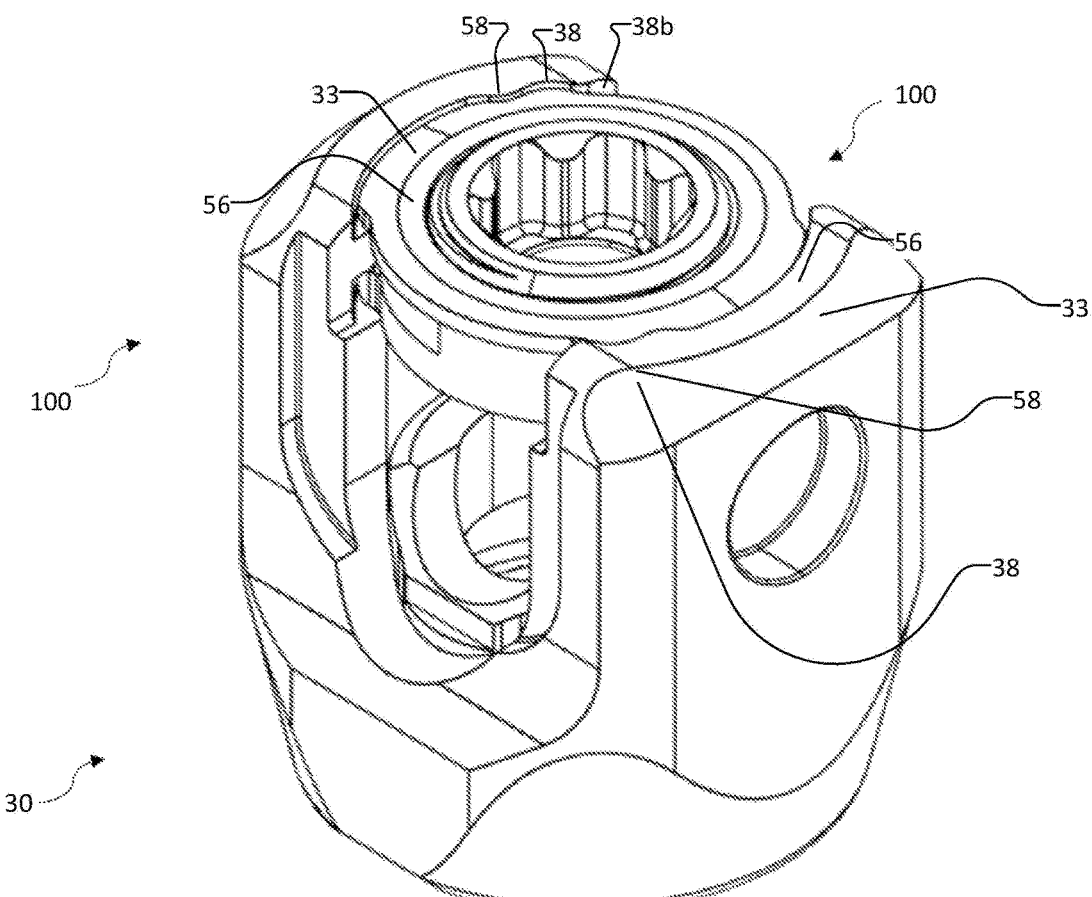
FIG. 7A is a perspective view of an example locking-cap system after being engaged in a locking position.
Figure 7B:
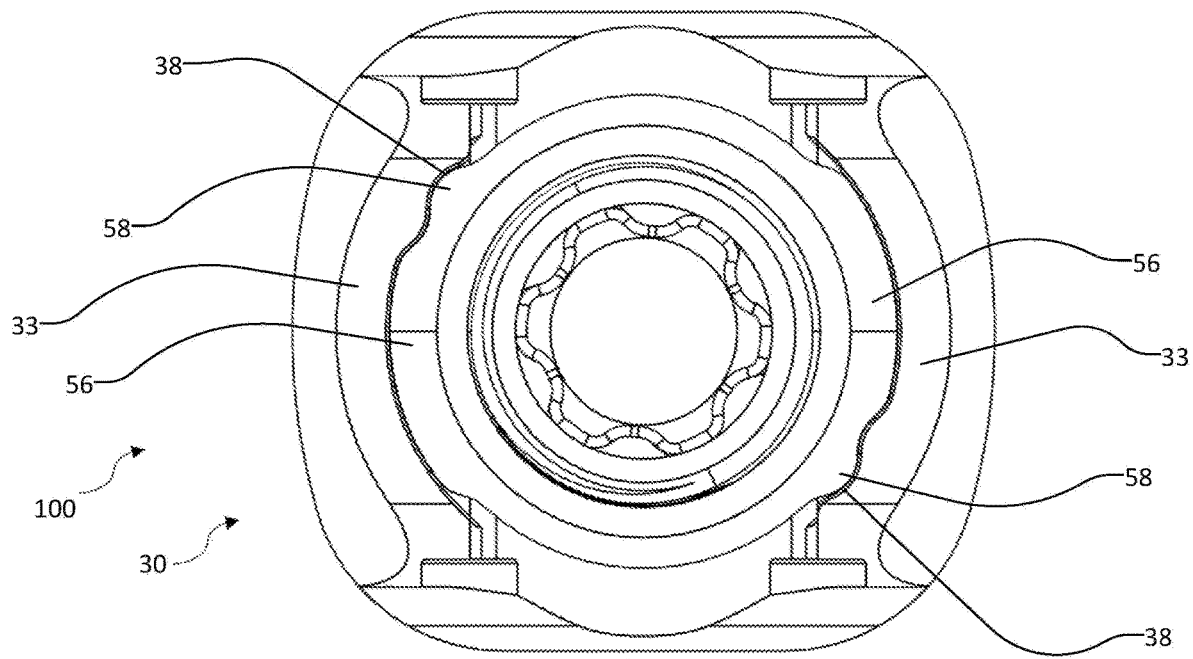
FIG. 7B is a top down view of an example locking-cap system after being engaged in a locking position.

FIG. 7A is a perspective view of an example locking-cap module 100 after being engaged in the locking position. FIG. 7B is a top down view of an example locking-cap module 100 after being engaged in the locking position. As illustrated, the rails 54, connecting flanges 56, and locking feature 58 may be selectively engaged with the connecting portion 30c of connector 30. In the example embodiment, each rail 54 may be mated to and/or positioned within a corresponding lower channel 34 of connector 30 and each connecting flange 56 may be mated to and/or positioned within a corresponding upper channel 36. Furthermore, each locking feature 58 may be mated to and/or positioned within indent 38.

In practice, an end user such as a surgeon may first position a pre-loaded locking module 100 in the initial position as shown in FIGS. 6A and 6B. Thereafter, the end user may rotate the locking-cap module 100 clockwise by engaging a driver or a rotation instrument with the drive feature 64 of set screw 60. As previously explained, the locking-cap 50 and set screw 60 may be initially coupled by a pre-loaded connection. Therefore, by applying a rotational force to set screw 60 the locking-cap module 100 (including the locking-cap 50 and set screw 60) may be positioned in the locking position. In some embodiments, just before fully positioning the locking-cap module 100 in the locking position, the locking-cap module 100, via the locking feature 58 may contact the outdent 38a and experience some rotational resistance. The end user may apply a sufficient rotational force to set screw 60 to overcome the rotational resistance thereby seating each locking feature 58 of locking-cap 50 in the corresponding indent 38 of the connector 30. In some embodiments, the sufficient rotational force required to seat the locking-cap 50 in the locked position is around 1.2 Nm or about 10.62 in-lbs. of torque. In other embodiments, the sufficient rotation force ranges from about 0.75 Nm to 1.5 Nm. At least one advantage of this configuration, is that when the locking-cap 50 is engaged with the connector 30 in the locked position, the locking features 58 are visibly verifiable to an end user as being in the locked position.

Afterwards, an end user may continue to apply a rotational force to set screw 60 to advance set screw 60 downward along axis A-A towards a longitudinal rod 20 (not illustrated in FIGS. 7A and 7B). The locking-cap 50 may be prevented from further rotation due to a stopping feature 38b, for example. Stopping feature 38b may protrude from connector 30 towards axis A-A and be disposed adjacent indent 38, for example. Due to the stopping feature 38b, the locking-cap 50 may be prevented from further rotating out of the locked position. Additionally, by continuing to apply a rotational force to set screw 60, the pre-loaded connection between set screw 60 and locking-cap 50 may be overcome and/or broken, for example. After the pre-loaded connection between set screw 60 and locking-cap 50 is broken, an end user may continue to rotate set screw 60 and advance set screw 60 along axis A-A until it directly contacts a longitudinal rod 20 positioned thereunder. In doing so, the locking-cap 50 may securely retain the set screw 60 relative to connector 30 and the set screw 60 may securely retain a longitudinal rod 20 relative to connector 30. Furthermore, if the end user or surgeon needed to reposition the longitudinal rod 20, the end user may back the set screw 60 out due to the locking-cap 50 being seated in the locked position and the pre-loaded connection being broken.

Additionally, in some embodiments, the first thread pattern 52 of the locking-cap 50 and/or the thread pattern 62 of the set screw 60 may include a run-out-portion where the threads and/or the thread pitch terminates or runs out, for example. In some embodiments, the run-out-portion may be configured to prevent the set screw 60 from threading through the locking-cap 50. Additionally, in some embodiments, the run-out-portion may also be configured to maintain the set screw 60 in an optimal position to accept and retain the longitudinal rod 20 within the rod passageway of the connector 30.

Figure 8:
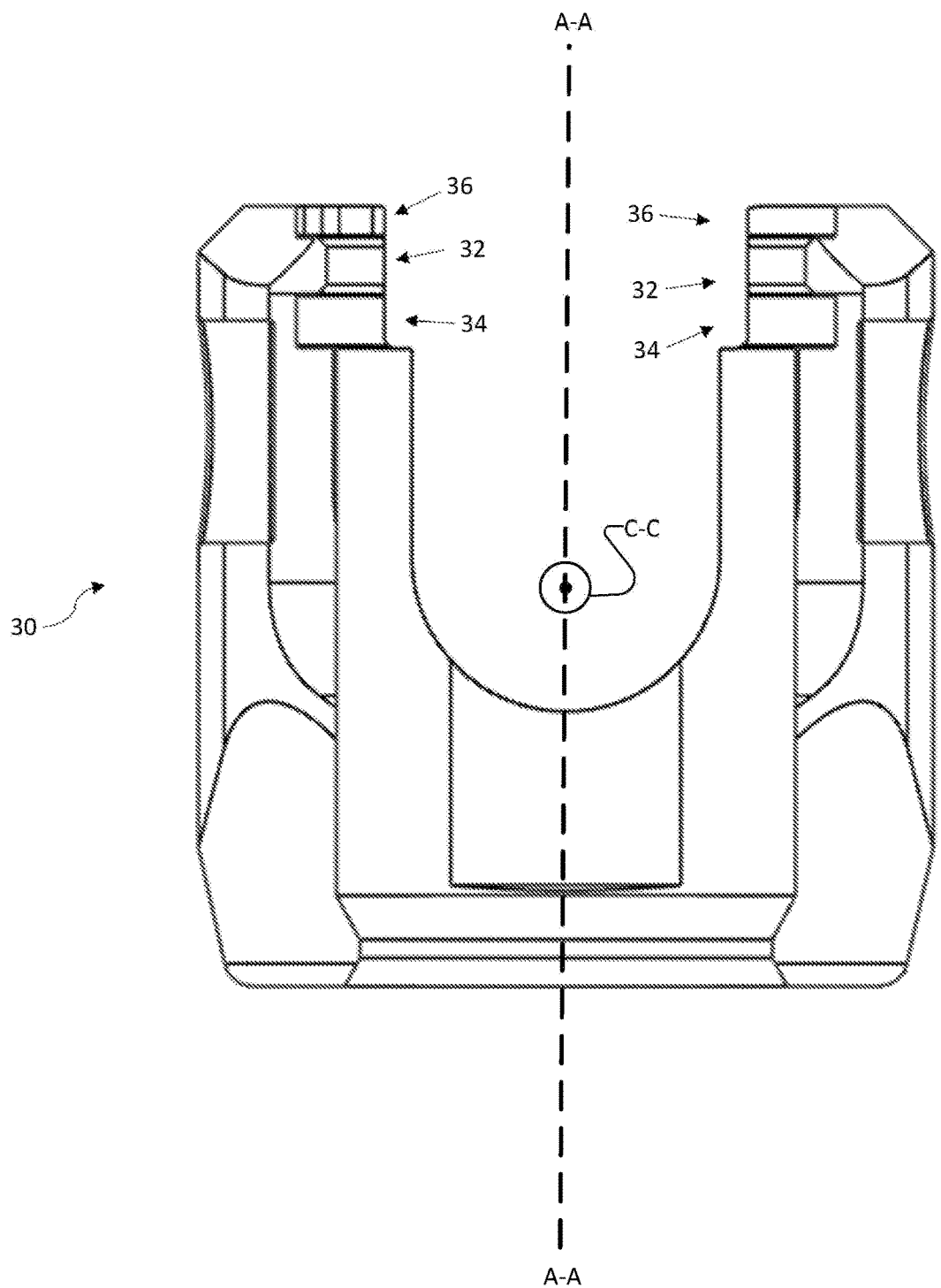
FIG. 8 is a cross sectional view of an example connector.

FIG. 8 is a cross sectional view of an example connector 30. In the example embodiment of FIG. 8, connector 30 is shown in cross section to further illustrate connecting rail 32 being disposed between the lower connecting channel 34 and upper connecting channel 36. Additionally, connector 30 may define a rod passageway configured to orient a longitudinal rod 20 along axis C-C. Consistent with the above disclosure, axis C-C may be further defined by the combination of connector 30, crown 40, and locking-cap 50. It shall also be understood that the specific location of axis C-C is not shown to scale and the exact location of axis C-C relative to connector 30 may be different, i.e., axis C-C is shown only for illustrative purposes. Furthermore, when the longitudinal rod 20 is placed in the rod passageway, axis B-B defined by the longitudinal rod itself may be coextensive with axis C-C defined by connector 30 and locking-cap 40, for example.

Figure 9:
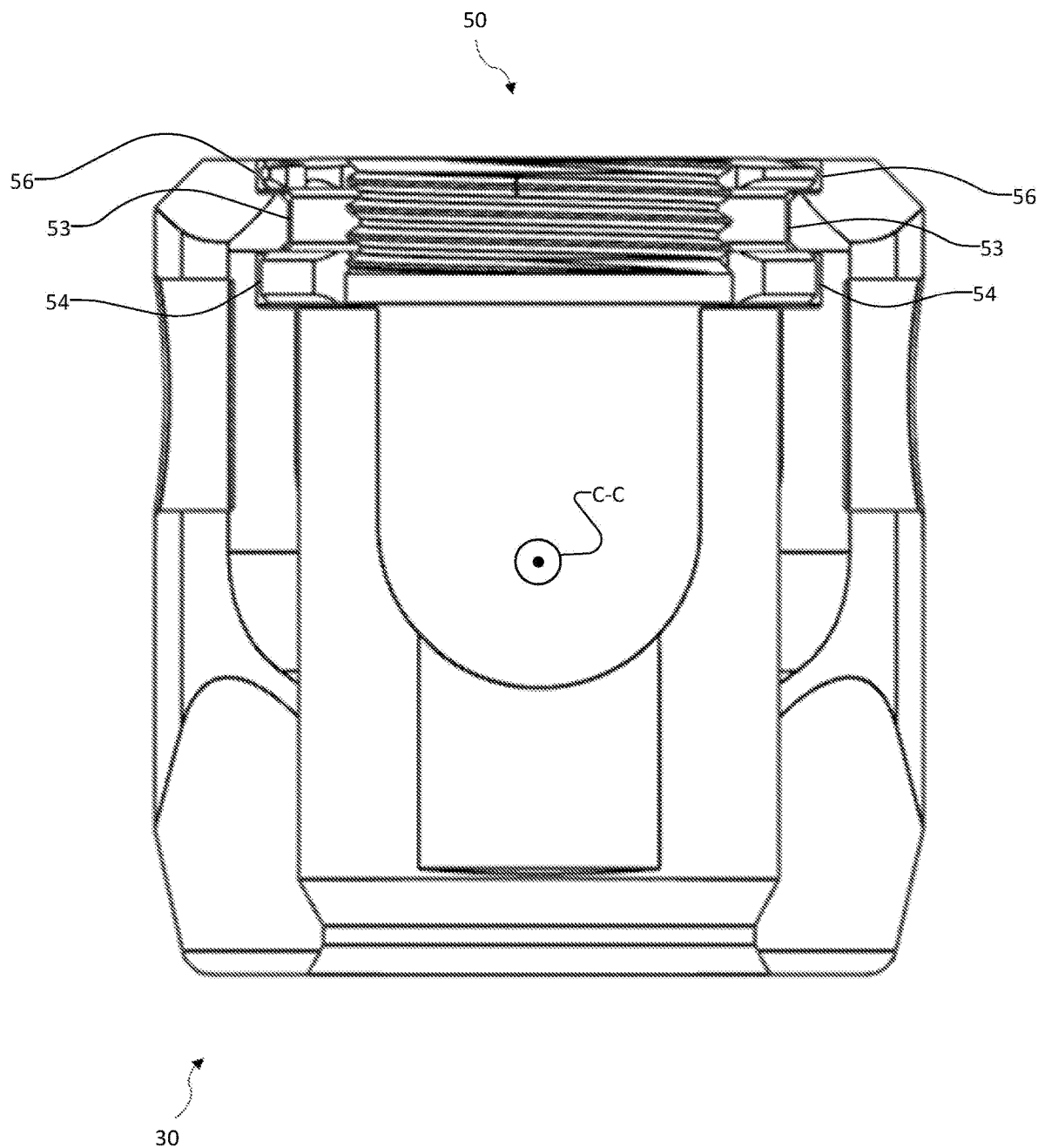
FIG. 9 is a cross sectional view of an example connector and an example locking-cap engaged in a locking position.

FIG. 9 is a cross sectional view of an example connector 30 and an example locking-cap 50 engaged in a locking position. In the example embodiment of FIG. 9, connector 30 and locking-cap 50 are shown in cross section to illustrate flanges 56 being seated within the upper connecting channel 36 and rails 54 being seated within the lower connecting channel 34, for example. Additionally, it is shown that connecting rail 32 of connector 30 is seated between flanges 56 and rails 54 in the recessed portion 53, for example.

Figure 10:
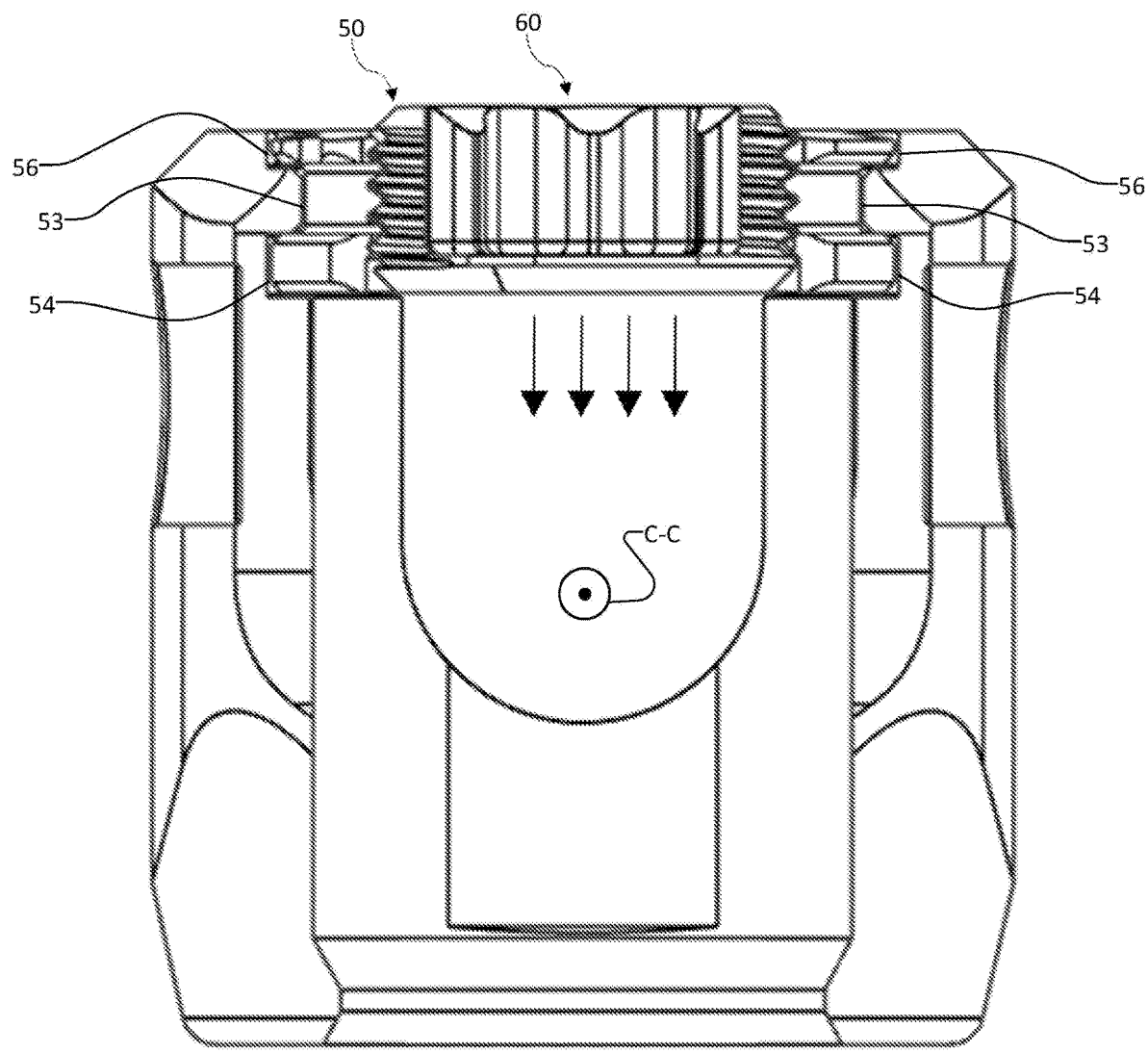
FIG. 10 is a cross sectional view of an example connector, an example locking-cap, and an example set screw engaged in a locking position.

FIG. 10 is a cross sectional view of an example connector 30, an example locking-cap 50, and an example set screw 60 engaged in a locking position. As illustrated, set screw 60 may rotated within locking-cap 50 and advance towards axis C-C. Set screw 60 may apply a downward force (represented by arrows) against a longitudinal rod 20 (not illustrated) that is axially aligned with axis C-C. When set screw 60 is sufficiently tightened against longitudinal rod 20 and applies a downward compressive force against longitudinal rod 20 a return force may be applied upward through set screw 60 and connector 50 at the junction between a top surface of the lower rail 54 of locking-cap 50 and a bottom surface of the rail 32 of connector 30, for example. In this way, the locking-cap 50 may enable the set screw 60 to apply a sufficient downward retaining force against a longitudinal rod 20 while also maintaining a relatively low total height of connector 30. For example, connector 30 may about 13.5 mm in height whereas other connectors relying on threads as opposed to locking-caps may be relatively greater in height. As the set screw 60 is tightened and force is applied as explained above, the locking-cap 50 may experience forces that could cause it to bend, flex, or bow. However, due to the flanges 56 being seated generally flush with the top surface of connector 30, the locking-cap 50 may be prevented from bending, flexing, or bowing. In experimental testing, this arrangement has been shown to exhibit relatively significant strength improvements over other designs due to the flanges 56 being constrained laterally and therefore unable to bend, bow, or flex.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:
1. A locking-cap module, comprising:
  a locking-cap including:
    an internal circumferential surface having a first thread pattern formed thereon; and
    a protruding engagement structure extending out and away from a top portion of an exterior sidewall of the locking cap so as to at least partially define a top surface of the locking-cap, the protruding engagement structure comprising
      at least one connecting flange;

a locking feature spaced apart from the at least one connecting flange in a lateral direction by a distance; and
a first indent located between the at least one connecting flange and the locking feature; and
at least one retaining rail extending out and away from a bottom portion of the sidewall of the locking-cap and defining, at least partly, a bottom surface of the locking-cap;
a set screw disposed in a central opening formed through the locking-cap, the set screw comprising an external circumferential surface having a second thread pattern formed thereon that is configured to threadingly engage the first thread pattern of the locking-cap; and
a mechanical non-threaded coupling provided between the locking cap and the set screw to cause temporary simultaneous rotation thereof when the locking-cap is being transitioned from an unlocked position relative to a connector to a locked position relative to the connector, the mechanical non-threaded coupling configured to be discontinued when (1) the locking feature resides in a second indent formed in a connector, (2) the first indent has a protruding member of the connector residing therein, and (3) torque is being applied to the set screw;
wherein the top surface of the locking-cap is flush with a top surface of the connector when in the locked and unlocked positions, and a top surface of the set screw is level with the top surface of the connector before (1) and (2) occur and unlevel with the top surface of the connector after (1) and (2) occur.

2. The locking-cap module of claim 1, wherein the protruding engagement structure comprises a first connecting flange and a second connecting flange disposed opposite one another.

3. The locking-cap module of claim 2, wherein the locking feature comprises a curved outdent.

4. The locking-cap module of claim 3, wherein the locking feature is configured to facilitate visual verification that the locking-cap is in the locked position.

5. The locking-cap module of claim 1, wherein the mechanical coupling is discontinued when torque of 35 inch lbs. is applied to the set screw.

6. The locking-cap module of claim 1, wherein the first thread pattern and second thread pattern comprise a run-out-portion, the run-out-portion configured to prevent the set screw from threading through the locking-cap.

7. The locking-cap module of claim 6, wherein the run-out-portion is configured to maintain the set screw in a position such that the set screw directly contacts a longitudinal rod extending through a rod passageway of the connector.

8. A locking-cap system, comprising:
a locking-cap including:
an internal circumferential surface having a first thread pattern formed thereon;
a protruding engagement structure extending out and away from a top portion of an exterior sidewall of the locking cap so as to at least partially define a top surface of the locking-cap, the protruding engagement structure comprising
at least one connecting flange,
a locking feature spaced apart from the at least one connecting flange in a lateral direction by a distance, and
a first indent located between the at least one connecting flange and the locking feature; and
at least one retaining extending out and away from a bottom portion of the sidewall of the locking-cap and defining, at least partly, a bottom surface of the locking-cap;
a set screw disposed in a central opening formed through the locking-cap, the set screw comprising an external circumferential surface having a second thread pattern formed thereon that is configured to threadingly engage the first thread pattern of the locking-cap;
a mechanical non-threaded coupling provided between the locking cap and the set screw to cause temporary simultaneous rotation thereof when the locking-cap is being transitioned from an unlocked position relative to a connector to a locked position relative to the connector, the mechanical non-threaded coupling configured to be discontinued when (1) the locking feature resides in a second indent formed in a connector, (2) the first indent has a protruding member of the connector residing therein, and (3) torque is being applied to the set screw; and
a connector including
an internal surface comprising a rod passageway and a connecting portion, the connecting portion configured to selectively couple with the locking-cap such that the locking-cap is fixed relative to the connecting portion when in the locked position;
wherein the top surface of the locking-cap is flush with a top surface of the connector when in the locked and unlocked positions, and a top surface of the set screw is level with the top surface of the connector before (1) and (2) occur and unlevel with the top surface of the connector after (1) and (2) occur.

9. The locking-cap system of claim 8, wherein the protruding engagement structure comprises a first connecting flange and a second connecting flange disposed opposite one another.

10. The locking-cap system of claim 9, wherein the locking feature comprises a curved outdent.

11. The locking-cap system of claim 10, wherein the locking feature is configured to facilitate visual verification that the locking-cap is in the locked position.

12. The locking-cap system of claim 8, wherein the mechanical coupling is discontinues when torque of 35 inch lbs. is applied to the set screw.

13. The locking-cap system of claim 12, wherein the first thread pattern and second thread pattern comprise a run-out-portion, the run-out-portion configured to prevent the set screw from threading through the locking-cap.

14. The locking-cap system of claim 13, further comprising:
a longitudinal rod;
a crown;
an anchoring member;
wherein the connector is secured to the anchoring member,
wherein the longitudinal rod extends through the rod passageway,
wherein the crown facilitates positioning of the longitudinal rod in the rod passageway, and
wherein the run-out-portion is further configured to maintain the set screw in a position to retain the longitudinal rod.

15. A method for operating a locking-cap module, comprising:
obtaining the locking-cap module having a set screw engaged with a locking-cap the locking-cap including:

a protruding engagement structure extending out and away from a top portion of an exterior sidewall of the locking cap so as to at least partially define a top surface of the locking-cap, the protruding engagement structure comprising
  at least one connecting flange,
  a locking feature spaced apart from the at least one connecting flange in a lateral direction by a distance, and
  a first indent located between the at least one connecting flange and the locking feature, and
at least one retaining rail extending out and away from a bottom portion of the sidewall of the locking-cap and defining, at least partly, a bottom surface of the locking-cap; and
transitioning the locking-cap from an unlocked position relative to a connector to a locked position relative to the connector;
using a mechanical non-threaded coupling provided between the locking cap and the set screw to cause temporary simultaneous rotation thereof as the locking-cap is being transitioned from the unlocked position to the locked position; and
causing the mechanical non-threaded coupling to be discontinued by applying torque to the set screw when (1) the locking feature resides in a second indent formed in a connector and (2) the first indent has a protruding member of the connector residing therein;
wherein the top surface of the locking-cap is flush with a top surface of the connector when in the locked and unlocked positions, and a top surface of the set screw is level with the top surface of the connector before (1) and (2) occur and unlevel with the top surface of the connector after (1) and (2) occur.

16. The method of claim 15, further comprising:
installing an anchoring member in a boney structure of a patient;
securing the connector to the anchoring member;
positioning a crown within the connector;
positioning a longitudinal rod within a rod passageway of the connector on top of the crown; and
rotating the set screw, after overcoming the pre-loaded connection, thereby securing the longitudinal rod with the rod passageway.

\* \* \* \* \*